United States Patent [19]

Horn

[11] Patent Number: 5,614,655
[45] Date of Patent: Mar. 25, 1997

[54] GAS MIXING DEVICE

[75] Inventor: Horst Horn, Springe/Bundesrepublik, Germany

[73] Assignee: Siemens Aktiengesellschaft, München, Germany

[21] Appl. No.: 522,272

[22] PCT Filed: Mar. 4, 1994

[86] PCT No.: PCT/DE94/00240

§ 371 Date: Sep. 11, 1995

§ 102(e) Date: Sep. 11, 1995

[87] PCT Pub. No.: WO94/20851

PCT Pub. Date: Sep. 15, 1994

[30] Foreign Application Priority Data

Mar. 12, 1993 [DE] Germany .......................... 93 03 693.0

[51] Int. Cl.⁶ .................................................. F16K 19/00
[52] U.S. Cl. ................................................................ 73/1 G
[58] Field of Search .............................. 73/1 G; 137/602, 137/605–607, 896, 897, 597, 599

[56] References Cited

U.S. PATENT DOCUMENTS

| 3,830,256 | 8/1974 | Cox ............................................ 137/599 |
| 4,256,100 | 3/1981 | Levy et al. ................................. 137/599 |
| 4,313,456 | 2/1982 | Holzem et al. ............................. 137/599 |
| 4,498,496 | 2/1985 | Barcellona et al. ........................ 73/1 G |
| 4,989,637 | 2/1991 | Dittrich ...................................... 137/606 |
| 5,239,856 | 8/1993 | Mettes et al. ............................... 73/1 G |
| 5,261,452 | 11/1993 | McAndrew et al. ....................... 73/1 G |
| 5,436,165 | 7/1995 | Bienner . |

FOREIGN PATENT DOCUMENTS

| 0370151 | 5/1990 | European Pat. Off. . |
| 0519783 | 12/1992 | European Pat. Off. . |
| 2904872 | 8/1980 | Germany . |
| 2036370 | 6/1980 | United Kingdom . |

OTHER PUBLICATIONS

AMEC AG Wangen, Switzerland, Comtomer Information, May 14, 1987.

Technisches Messen 59 (1992) 2, R. Oldenbourg Verlag: *Rechnergestützte Kalibrierung von Gasanalysegeräten (Computer–aided Calibration of Gas Analyers)*, A. Slemeyer et al.

*Primary Examiner*—Robert Raevis
*Attorney, Agent, or Firm*—Kenyon & Kenyon

[57] ABSTRACT

A gas distributor with critical nozzles is proposed, the nozzle cross-sections increasing by 1:2 from one to the next, and each of these nozzles being capable of admitting either a test gas or a zero gas. With four nozzles of this type, 16 linearly graduated concentrations of the test gas in the zero gas are obtained.

15 Claims, 1 Drawing Sheet

GAS MIXING DEVICE

BACKGROUND OF THE INVENTION

The present invention relates to a gas mixing devices in general and more particularly to improved apparatus for calibrating gas analyzers comprised of a plurality of critical nozzles which have their outputs connected to a mixing chamber.

Known gas mixing devices, also called gas distributors, use eleven or eight critical nozzles to obtain eleven or seventeen different concentrations or selectively variable proportions. At a specific input gas pressure, because of a special shaping of their outlet ports, these nozzles provide a constant gas passage that remains dependent only on the opening cross-section. Nozzles of this type require precision manufacturing and exact measuring.

Because of this last requirement there is a need to increase the ratio between the number of selectively variable proportions and the number of critical nozzles required for this purpose, so that one can make do with a smaller number of critical nozzles.

SUMMARY OF THE INVENTION

This need is fulfilled in accordance with the present invention by providing a plurality of critical nozzles having their outputs connected to a mixing chamber with the cross-sections of each critical nozzles increasing in the proportion of 1:2 from one to the next, and permitting each critical nozzle to receive either a test gas or a zero gas.

The present invention makes it possible to reduce the number of required critical nozzles at least by half and to give the gas mixing device a considerably more compact design.

In accordance with the illustrated embodiment a valve having two inlets capable of being alternatively opened is placed upstream from each critical nozzle. A remotely controllable, electromagnetic actuation of the valves is provided. The valves may be provided with a position transducer. In the illustrated embodiment, four nozzles, whose cross-sections are in proportions of 1:2:4:8, are provided. The nozzle with the largest cross-section is arranged opposite the output of the mixing chamber. Furthermore, as illustrated, a microprocessor is provided as a control computer to activate the valves, as well as to monitor and regulate the gas pressures. The microprocessor is provided with a communication line leading to a host computer superordinate to said microprocessor.

DETAILED DESCRIPTION

Figure 1:
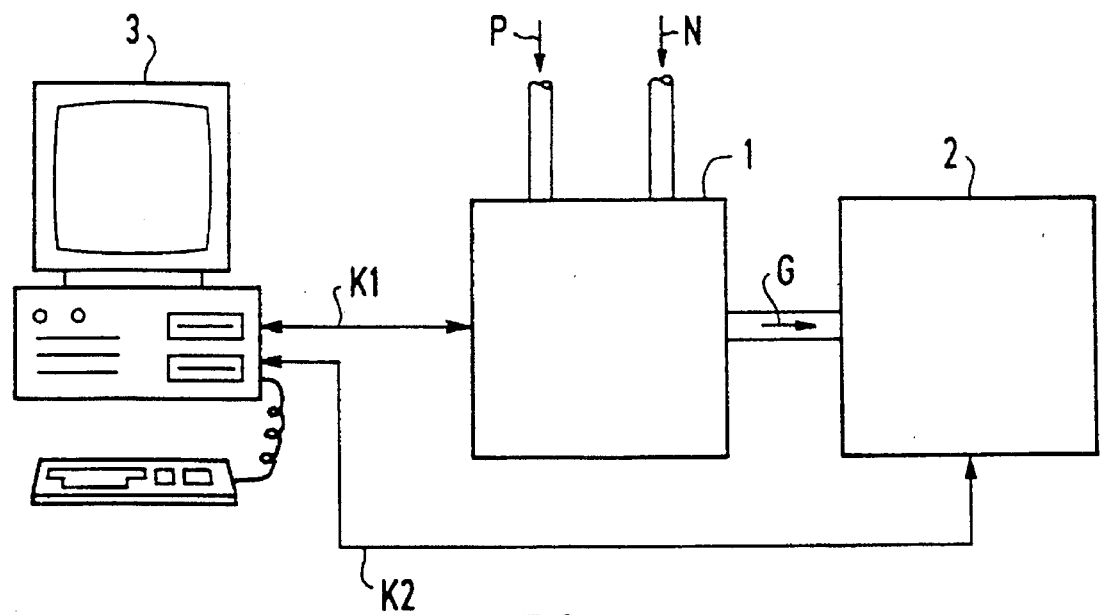
FIG. 1 is a gas mixing device in an arrangement for the computer-supported calibration of a gas analyzer.

In FIG. 1 a gas mixing device or distributor 1, which is integrated in a generally known arrangement for the computer-supported calibration of a gas analyzer 2 is shown. A so-called zero gas N, also denoted as carrier gas or diluent gas, as well as the test gas P, also called a calibration gas, are supplied via piping to the gas mixing device. The gas distributor 1 and the gas analyzer 2 each have an interface, as a rule a serial interface, together with corresponding communication lines K1 or K2 leading to a host computer 3. The gas analyzer 2 is calibrated by means of a program, which is loaded in the working storage of the computer 3 and which prescribes to the gas distributor 1 discrete concentrations of test gas and zero gas, one after another, for the gas mixture G to be supplied to the analyzer 2. Then, for every adjustment of the gas mixture, it logs the concentration value measured by the analyzer 2. The purpose of such a calibration is determining the correlation valid for a given measuring device between the measured value specified by it and the correct value of the measurable parameter, which is adjusted as a standard measure by means of the gas distributor 1.

Figure 2:
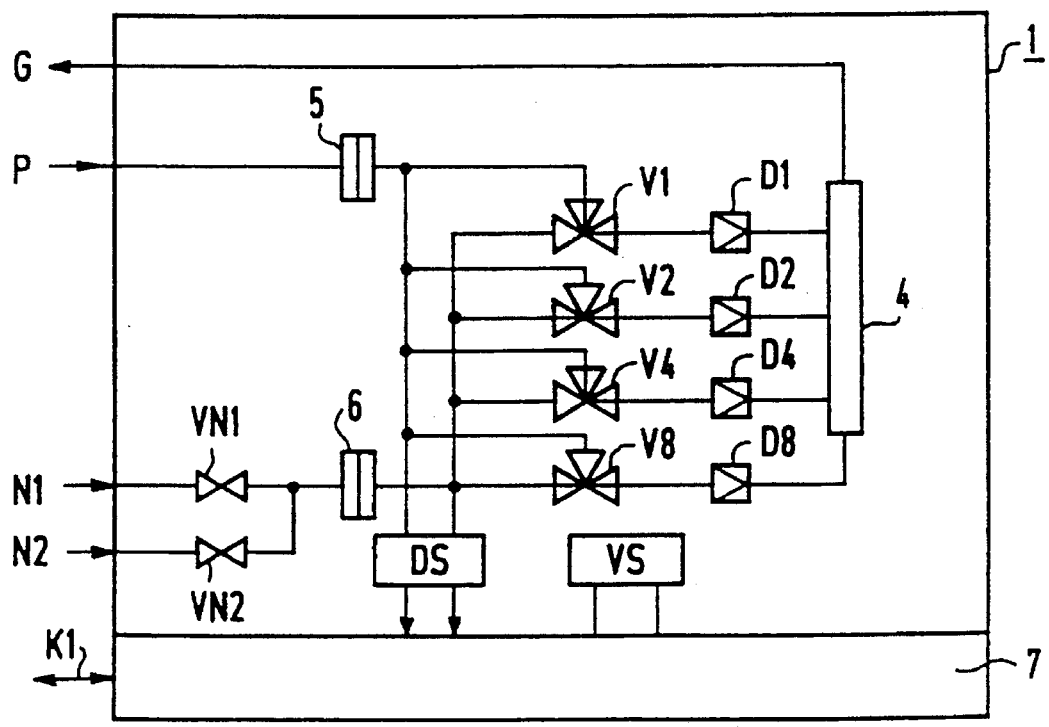
FIG. 2 is a block diagram of the gas mixing device according to the present invention.

In the block diagram of the gas distributor according to the present invention in accordance with FIG. 2, a mixing chamber 4 is shown, in which the gas streams flowing through the nozzles D1, D2, D4 and D8 mix and emerge as a gas mixture G out of the gas distributor 1. The nozzles D1 through D8 are supposed to be so-called critical nozzles, i.e., nozzles, which, as already mentioned, because of a special shaping of their outlet ports, at pressures above certain minimum pressure, i.e., the critical pressure, always result in a constant gas volume, which remains dependent only on the cross-section of the opening through which the gas passes. The cross-sections of the critical nozzles D1 through D8 are in proportions of 1:2:4:8. Placed upstream from the nozzles are four three-way valves V1, V2, V4 and V8, which open a path to a respective downstream critical nozzle either for the test gas P or for one of the zero gases designated by N1 and N2 that can be supplied optionally via the valve VN1 or VN2. Thus, utilizing all possible nozzle combinations, 15 distributor proportions, i.e., including the concentration proportion zero, 16 discrete adjustments of the concentration of the test gas in the zero gas are possible.

The zero gases can be nitrogen or artificial atmosphere, for example. Filters 5 and 6 prevent contamination of the nozzles. The gas pressures of the test gas P and of the supplied zero gas are detected by a pressure sensor DS and relayed to a microprocessor 7 serving as a control computer, which in a generally known manner assures that the gas pressures of the test gas and of the zero gas each lie above the mentioned critical pressure. Moreover, in proportion to the adjustment value communicated to the microprocessor via the communication line K1, the microprocessor effects a proper actuation of all valves via the valve drive circuit VS indicated as a functional block. It is expedient to equip the valves with a position transducer, so that the microprocessor 7 can monitor whether the adjustment of the valves specified by it is also actually undertaken. The valves are expediently actuated electromagnetically, for example by means of a coil drive. In the case of the adjustment assumed in FIG. 2, the operating coil of the valves V2 and V8 is currentless, so that the path for the zero gas N1 or N2 through these valves is open, and the operating coils of the valves V1 and V4 are excited, so that these valves are traversed by the flow of the test gas P. Thus, a concentration of the test gas P in the gas mixture G of 5:15 or 33.33% results.

The selected graduation of the cross-sections of the critical nozzles, namely successively, always in a proportion of 1:2, and the alternative admitting always of one of the two gases into the nozzles, leads to a minimum number of nozzles to be held ready, given linearly graduated concentrations. A similarly favorable ratio between the number of selectively variable proportions and the number of critical nozzles required for this would also result, for example, with three critical nozzles, whose opening cross-sections are in proportions of 1:2:4 and which, in the case of the type of admitting in accordance with the present invention, make it possible to realize eight concentration proportions.

The mixing-chamber inlets associated with the nozzles can be configured in any desired manner. It is recommended that the inlet, which is associated with the nozzle D8 having the highest rate of flow be arranged opposite the output of the mixing chamber 4. Thus, during the rinsing operation, in which zero gas is admitted into all the nozzles, the very smallest residues of test gas remaining in the mixing chamber due to earlier calibrations are rinsed out very quickly.

I claim:

1. A gas mixing device comprising:
   a. a mixing chamber; and
   b. a plurality of critical nozzles having their outputs connected to said mixing chamber, the cross-sections of said critical nozzles increasing by a proportion of 1:2 from one to the next, and each critical nozzle having inputs to receive either a test gas or a zero gas, wherein said plurality of critical nozzles comprise four nozzles whose cross-sections are in proportions of 1:2:4:8.

2. The device according to claim 1, wherein said inputs to receive either a test gas or a zero gas comprise a plurality of valves, each having two inlets, said inlets capable of being alternatively opened, one of said valves disposed upstream from each critical nozzle.

3. The device according to claim 2, wherein the nozzle with the largest cross-section is disposed opposite the output of said mixing chamber.

4. The device according to claim 2, and further including a microprocessor coupled to activate the valves, said microprocessor also monitoring and regulating the gas pressures.

5. The device according to claim 4, and further including:
   a. a host computer;
   b. a communication line coupling said microprocessor to said host computer.

6. The device according to claim 2, wherein said valves are remotely controllable, electromagnetically actuated valves.

7. The device according to claim 6, wherein the nozzle with the largest cross-section is disposed opposite the output of said mixing chamber.

8. The device according to claim 6 and further including a position transducer for each valve.

9. The device according to claim 8, wherein the nozzle with the largest cross-section is disposed opposite the output of said mixing chamber.

10. The device according to claim 2 and further including a position transducer for each valve.

11. The device according to claim 10, wherein the nozzle with the largest cross-section is disposed opposite the output of said mixing chamber.

12. The device according to claim 1, and further including a microprocessor coupled to activate the valves, said microprocessor also monitoring and regulating the gas pressures.

13. The device according to claim 12, and further including:
    a. a host computer;
    b. a communication line coupling said microprocessor to said host computer.

14. The device according to claim 1, wherein the nozzle with the largest cross-section is disposed opposite the output of said mixing chamber.

15. The device according to claim 1, wherein the nozzle with the largest cross-section is disposed opposite the output of said mixing chamber.

* * * * *